(12) United States Patent
Chou

(10) Patent No.: US 10,265,575 B2
(45) Date of Patent: Apr. 23, 2019

(54) EXERCISE MACHINE WITH ANALYSIS SYSTEM

(71) Applicant: Cheng I. Chou, City of Industry, CA (US)

(72) Inventor: Cheng I. Chou, City of Industry, CA (US)

(\*) Notice: Subject to any disclaimer, the term of this patent is extended or adjusted under 35 U.S.C. 154(b) by 113 days.

(21) Appl. No.: 15/339,905

(22) Filed: Oct. 31, 2016

(65) Prior Publication Data

US 2017/0165523 A1 Jun. 15, 2017

Related U.S. Application Data

(60) Provisional application No. 62/245,294, filed on Oct. 23, 2015.

(51) Int. Cl.

| | | |
|---|---|---|
| *A61B 5/00* | (2006.01) | |
| *A63B 24/00* | (2006.01) | |
| *A61B 5/11* | (2006.01) | |
| *A63B 22/02* | (2006.01) | |
| *A63B 23/04* | (2006.01) | |
| *A61B 5/103* | (2006.01) | |
| *A63B 22/06* | (2006.01) | |
| *A63B 71/06* | (2006.01) | |

(52) U.S. Cl.
CPC ............ *A63B 23/0405* (2013.01); *A61B 5/00* (2013.01); *A61B 5/112* (2013.01); *A61B 5/6895* (2013.01); *A63B 22/025* (2015.10); *A63B 22/0242* (2013.01); *A63B 24/0087* (2013.01); *A61B 5/1036* (2013.01); *A61B 2505/09* (2013.01); *A63B 22/0605* (2013.01); *A63B 71/0619* (2013.01); *A63B 2024/0093* (2013.01); *A63B 2220/17* (2013.01); *A63B 2220/20* (2013.01); *A63B 2220/30* (2013.01); *A63B 2220/52* (2013.01); *A63B 2225/50* (2013.01); *A63B 2230/01* (2013.01); *A63B 2230/75* (2013.01)

(58) Field of Classification Search
CPC . A63B 24/00; A63B 24/0062; A63B 24/0087; A63B 2225/50; A63B 2024/0093; A63B 22/0605; A63B 5/00; A63B 2230/75; A63B 2230/01; A63B 2220/20; A63B 2230/30; A63B 2230/17; A63B 23/0405
See application file for complete search history.

(56) References Cited

U.S. PATENT DOCUMENTS

| | | | | |
|---|---|---|---|---|
| 4,625,962 A | * | 12/1986 | Street | A63B 21/015 482/116 |
| 2002/0045517 A1 | * | 4/2002 | Oglesby | A63B 22/0023 482/51 |
| 2009/0251296 A1 | * | 10/2009 | Whelan, Jr. | A63B 21/0053 340/10.51 |
| 2010/0210418 A1 | * | 8/2010 | Park | A63B 21/0053 482/4 |
| 2011/0312474 A1 | * | 12/2011 | Ellis | A63B 21/0615 482/54 |
| 2012/0264569 A1 | * | 10/2012 | Escobedo | A63B 22/0023 482/5 |
| 2013/0274066 A1 | * | 10/2013 | Ashby | A63B 24/0087 482/4 |

\* cited by examiner

*Primary Examiner* — Joshua Lee
(74) *Attorney, Agent, or Firm* — Raymond Y. Chan; David and Raymond Patent Firm

(57) ABSTRACT

An exercise machine includes a motor that drives a belt to move, and an analysis system to collect a peak energy from the motor and to convert the peak energy into different user exercising data.

6 Claims, 1 Drawing Sheet

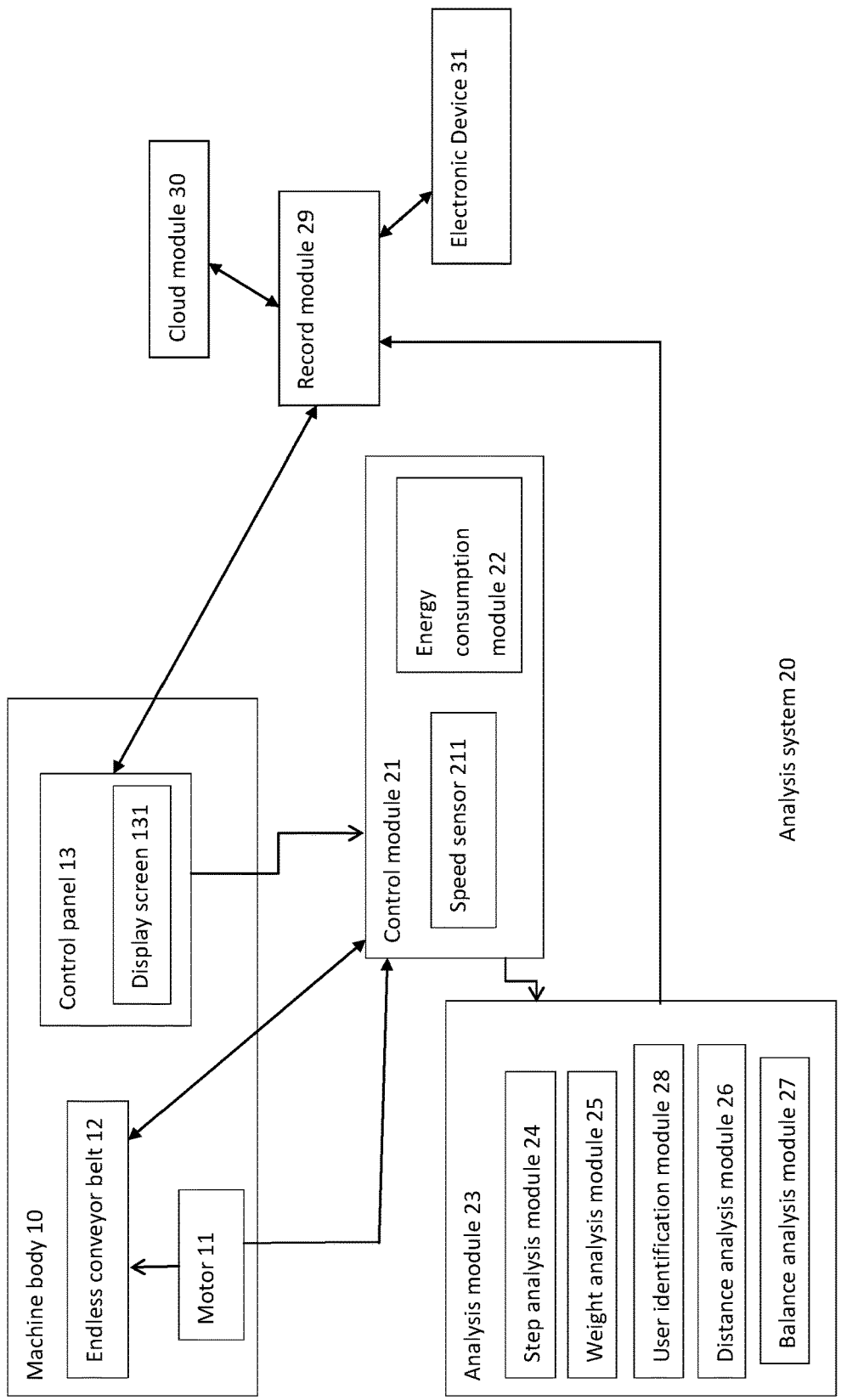

EXERCISE MACHINE WITH ANALYSIS SYSTEM

CROSS REFERENCE OF RELATED APPLICATION

This is a non-provisional application that claims priority to U.S. provisional application, application No. 62/245,294, filed Oct. 23, 2015, the entire contents of each of which are expressly incorporated herein by reference.

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to an exercise machine, and more particularly to an exercise machine with analysis system to convert signals into user exercise results data.

Description of Related Arts

A conventional exercise machine, such as a treadmill, usually comprises a running platform for the user walking or running thereon, wherein the running platform is configured to have a conveyor belt. People tend to walk or run on the conveyor belt of the treadmills to not only keep their shapes but also to get a cardio workout. While the users are walking and running on the conveyor belt, the users can set the speed and personal data, such as personal weights and heights, to the treadmill via a control module. Through the control module, the conventional treadmills can calculate exercise results, such as the calories lose or walking/running distance, based on the pre-set speed and personal information. However, the conventional treadmills have several drawbacks.

The exercise results provided by the conventional treadmills are imprecise. Most of the users cannot completely follow the speed of the conveyor belt, and when the users lose their balance on the conveyor belt or even if they are no longer walking or running thereon, the conventional treadmills cannot detect that. Therefore, the exercise results are usually non-objective, and not in a real time manner.

In addition, additional detection devices are able to incorporate with the conventional treadmill in order to provide more analysis functions, wherein the detection devices can be wearable devices worn on any portion of the user's bodies, such as smart phones or PDAs. The detection devices can be wirelessly connected with the conventional treadmills and provide step count functions, and further provide more accuracy exercise results, such as calories lose, walking/running speed, heart rate, walking/running distance, and so forth, so that the real time exercise conditions of the users are detected by the wearable devices. However, the detection devices are usually very expensive, and need to be charged by and connected with an output device, such as a computer, to display the exercise results, so that the users need to spend lots of times to obtain their exercise results. In addition, it is inconvenient and uncomfortable for the users to carry out the detection devices while they are walking or running on the exercise machine. Furthermore, once the users forget to bring their detection devices, the users will lose changes to record their exercise results this time.

SUMMARY OF THE PRESENT INVENTION

The invention is advantageous in that it provides an exercise machine with an analysis system which can convert motor output signals into different users' exercising data.

Another advantage of the invention is to provide an exercise machine with an analysis system, wherein the analysis system comprises a control module having a speed sensor to detect a speed of the user running/waling on an endless conveyor belt.

Another advantage of the invention is to provide an exercise machine with an analysis system, wherein the control module can determine the peak energy to a motor in order to drive the endless conveyor belt being operated at a constant speed in response to the dragging force thereat.

Another advantage of the invention is to provide an exercise machine with an analysis system, wherein the analysis system comprises a weight analysis module and a user identification module linked with the weight analysis module, so that the weight analysis module can identify the user weight and the user identification module can identify which user is running/walking on the endless conveyor belt.

Another advantage of the invention is to provide an exercise machine with an analysis system, wherein the analysis system comprises a balance analysis module adapted to measure the balance between the right foot and left foot of the user at each step on the belt.

Another advantage of the invention is to provide an exercise machine with an analysis system, wherein the analysis system comprises a distance analysis module to calculate the total distance of the user running/walking on the endless conveyor belt.

Another advantage of the invention is to provide an exercise machine with an analysis system, wherein the analysis system comprises a step analysis module to calculate total number of steps of the user running/walking on the endless conveyor belt.

Another advantage of the invention is to provide an exercise machine with an analysis system, wherein the analysis system comprises a record module wirelessly and selectively linked with a cloud module and an electronic device to transmit the exercise results data to the cloud and the electronic device, and then the exercise result data can be processed by process software of the cloud module and the electronic device.

Additional advantages and features of the invention will become apparent from the description which follows, and may be realized by means of the instrumentalities and combinations particular point out in the appended claims.

According to the present invention, the foregoing and other objects and advantages are attained by an exercise machine with an analysis system, comprising:

a machine body; and a control module having a speed sensor operatively linked with the machine body to convert signals into different user exercise result data.

Still further objects and advantages will become apparent from a consideration of the ensuing description and drawings.

These and other objectives, features, and advantages of the present invention will become apparent from the following detailed description, the accompanying drawings, and the appended claims.

BRIEF DESCRIPTION OF THE DRAWINGS

FIG. 1 is a block diagram of an exercise machine with analysis system according to a preferred embodiment of the present invention.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Referring to FIG. 1 of the drawing, an exercise machine according to a preferred embodiment of the present invention is illustrated, wherein a user is able to run or walk on the exercise machine of the present invention as a treadmill. The exercise machine comprises a machine body 10 and an analysis system 20.

The machine body 10 generally comprises a control panel 13, a motor 11, and a running track operatively connected with the motor 11. According to the preferred embodiment, the running track is designed as an endless conveyor belt 12 operatively connected with the motor 11, wherein the motor 11 is able to generate a rotational power to transmit to the endless conveyor belt 12 in order to drive the endless conveyor belt 12 to move. The control panel 13 can adjustably set the rotational power of the motor 11 to maintain a constant speed for the endless conveyor belt 12. The user is able to run or walk on the endless conveyor belt 12 to do the exercise and maintain the cardio workout.

The analysis system 20 comprises a control module 21 which comprises an speed sensor 211 operatively linked with the motor 11, the endless conveyor belt 12 and the control panel 13, and an analysis module 23 operatively linked with the control module 21. The speed sensor 211 is arranged for detecting the speed of the endless conveyor belt 12 to generate a real time signal in a real time manner, and the real time signal generated by the speed sensor 211 is arranged to identify the current speed of the endless conveyor belt 12.

It is worth mentioning that the control panel 13 can send a pre-set speed signal to the motor 11 to generate the start the movement of the endless conveyor belt 12 based on the pre-set speed signal. The motor 11 will generate an initial energy to drive the endless conveyor belt 12 at the constant speed. Once the endless conveyor belt 12 is activated to move at the desired constant speed, the motor 11 will be stayed at an idle position for generating the constant initial energy to maintain the rotational power so as to maintain the endless conveyor belt 12 at the constant speed. It is worth mentioning that the motor 11 at the idle position refers to the endless conveyor belt 12 at the constant speed without the user running or walking on the endless conveyor belt 12 at the constant speed.

However, while the user is walking/running on the endless conveyor belt 12, each step of the user will generate a stopping force or a dragging force to decrease the speed of the endless conveyor belt 12. Then, the motor 11 requires consuming a peak energy to drag the endless conveyor belt 12 to move for maintaining the endless conveyor belt 12 at the pre-set constant speed.

Accordingly, the control module 21 further comprises an energy consumption module 22 to determine a value of the peak energy from the motor 11, so that the real-time speed signal and the pre-set speed signal are transmitted and collected to the energy consumption module 22. Preferably, the real time signal is detected by the speed sensor 211 in ⅒ second, so that while a value of the real time signal is below to that of the pre-set speed signal, the control module 21 is noticed by the energy consumption module 22 to determine how much peak energy the motor 11 needed to be generated to maintain the endless conveyor board 12 at the pre-set constant speed by the peak energy all the time. In other words, the peak energy is an additional energy added to the initial energy of the motor 11 because the motor 11 requires more energy to drag the endless conveyor belt 12 to move at the pre-set constant speed when the user runs or steps on the endless conveyor belt 12.

It is worth mentioning that the energy consumption module 22 can convert the peak energy from the motor 11 into other energy form, such as calories, such that the energy consumption module 22 can calculate how much calories the user burnt in response to the peak energy.

The value of the real-time speed signal and the value of the pre-set speed signal, are collected by the control module 21, and then the control module 21 will generate a feedback signal based on the value of the real-time speed signal and the value of the pre-set speed signal, wherein the feedback signal is transmitted to the analysis module 23.

It is worth mentioning that each step of the user can also be detected by the speed sensor 211 as the detection of the dragging force on the endless conveyor belt 12, such that the each step of the user provides a step signal to the speed sensor 211, and the speed sensor 211 will be collected together to combine with the feedback signal. In other words, the feedback signal includes a frequency of the step signal and a value of each step signal. In addition, the step signals are transmitted to the speed sensor 211 under a pattern, wherein while the right foot of the user steps on the endless conveyor belt 12, the step signal will be generated from the endless conveyor belt 12 to the speed sensor 211, and continuously the left foot of the user steps on the endless conveyor belt 12, another step signal will be generated from the endless conveyor belt 12 to the speed sensor 211. Therefore, the frequency of the speed signal is defined by a frequency of the steps provided by the user's right and left feet.

The analysis module 23 comprises a step analysis module 24, a weight analysis module 25, a distance analysis module 26, a balance analysis module 27, and a user identification module 28.

The step analysis module 24 is adapted to calculate total number of steps provided by the user, wherein the number of the step signal can be collected and calculated by the step analysis module 24. Each step signal is calculated to be a step, so a total number of step signals can be calculated as a total number of steps provided by the user. In addition, the step analysis module 24 can calculate total number of steps within a period of time. It is worth mentioning that the system will detect the foot falls on the machine body 10, via the step analysis module 24, to verify that the user is running on a treadmill, as an example. The verification can be sent directly to a could module 30 and/or sent to the electronic device 31, such as the smart phone or smart device, which then sends to the cloud module 30.

The balance analysis module 26 is arranged to measure a value of weight provided by each step of the user's right and left feet, wherein the step signal from each step includes the value of each step signal, so that the value of the step signal can be calculated to be the amount of forces provided by the user's right and left feet for the step balancing analysis. In other words, if the value of one of the step signal is larger than that of the continuous step signal, it can be determined that the right foot and the left foot of the user is in a un-balance situation, so the user can use this result to modify his/her workout habit.

The weight analysis module 25 is arranged to calculate a weight of each user, and the weight analysis module 25 is linked with the user identification module 28, and the weight of the user can be determined by feedback signal. For example, while a user is walking and running on the endless conveyor belt 12, the weight of the user can be determined by the weight analysis module 25, and then the user can name the name of the user based on the weight of the user through the control panel 13 of the machine body 10, such that the weight of the user is 1201b, and named as "User 1". And, while another user is running/walking on the endless conveyor belt 12, the weight of the user is determined as 1401b, and named as "User 2". Furthermore, the user identification module 28 is able to determine the user based on the weight of the user. According to the above mentioned example, while the "User 1" is running/walking on the endless conveyor belt 12, the weight of the user can be calculated based on the feedback signal, so if the weight is measured as "1201b", the user identification module 28 will automatically identify that the user is "User 1". In other words, while the weight if the user is measured as "1401b", the user is identified as "User 2".

It is worth to mentioning that the weight of the user is determined by the peak energy collected by the control module 21 and the speed of the user. The following equation is used to determine the kinetic energy of the object (user):

$$E_k = \frac{1}{2}mV^2$$

$E^k$: kinetic energy of an object (Joules)
M: Mass (kg)
V: velocity (m/s)

According to the above mentioned equation, $E_k$ is the peak energy from the motor 11 to the endless conveyor belt 12, and V is the speed of the user running or walking on the endless conveyor belt 12, so that M (mass/weight) of the user can be calculated through the above equation. Therefore, the user identification module 28 can identify which user is walking or running on the endless conveyor belt 12.

The distance analysis module 26 is able to calculate total distance for the user while he/she is running/walking on the conveyor belt 12. Since the equation for calculating the distance of a moving object is:

Distance=average velocity×time

Accordingly, the average velocity of the user can be determined by the speed sensor 211 of the control module 21, so that the distance of the user who is running/walking on the endless conveyor belt 12 within a period of time can be calculated.

It is worth mentioning that the analysis system 20 further comprises a record module 29 linked with the analysis module 23 to record exercise result data. The analysis module 23 can generate an exercise result signal, which includes total steps of the user running/walking on the endless conveyor belt 12 within a period of time, balance analysis results between the user's right and left foot, weights and user identification results of each user, and total distance while the user running/walking on the endless conveyor belt 12 within a period of time.

In addition, the record module 29 is wireless linked to the cloud module 30 and an electronic device 31, so that the exercise result data can be transmitted to the cloud module 30 or the electronic device 31, and the cloud module 30 and the electronic device 31 comprises built-in software to analysis and process the exercise result data. For example, the built-in software can process to exercise result data into various kinds of graphs, tables, or charts, so that the users can review their exercise results anytime via the cloud module 30 or the electronic device 31 all the time.

It is worth mentioning that the record module 29 can be operatively linked with a control panel 13. Preferably, the control panel comprises a display screen 131, which can be a touch screen, to display the exercise results, so that the users can review the exercise results directly through the display screen 131 of the control panel 13. In other words, the exercise records saved into the cloud module 30 and the electronic device 31 also can be read by the display screen 131 through the record module 29.

The present invention further provides an energy analyzing method for a treadmill, which comprises the following steps.

(1) Collect the peak energy from the motor 11 of the treadmill in response to the dragging force on the endless conveyor belt 12. The peak energy collection comprises the following steps.

(1.1) Determine the initial energy from the motor 11 to maintain the endless conveyor belt 12 at the constant speed when the motor 11 is in the idle position.

(1.2) Determine the additional energy from the motor 11 to maintain the endless conveyor belt 12 at the constant speed when the dragging force is applied on the endless conveyor belt 12, wherein the additional energy from the motor 11 is the peak energy.

(2) Analyze the peak energy to convert the peak energy into different exercising data. The exercising data can be the energy consumption of the user in form of calories, the number of steps, the step balancing analysis, the weight analysis, and/or the user weight identification.

Accordingly, the analysis system 20 can be installed in various kinds of exercise machines, not only limited to the treadmill. In particular, the analysis system 20 can be installed into any existing treadmill having the motor and endless conveyor belt, or can be built-in with any treadmill. The analysis system 20 can be installed into a stationary bike, wherein the analysis system 20 can perform the same function as that the analysis system 20 is installed into the treadmill. In other words, the analysis system 20 can be installed in any kinds of exercise machine to provide exercise analysis function.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An energy analyzing method for an exercise machine, which comprises the steps of:
   (a) collecting a peak energy from a motor of said exercise machine in response to a dragging force on a belt of said exercise machine, wherein said peak energy is collected by the steps of:
   (a.1) determining an initial energy from said motor to maintain said belt at a constant speed when said motor is in an idle position; and
   (a.2) determining an additional energy from said motor to maintain said belt at said constant speed when said dragging force is applied on said belt, wherein said additional energy from said motor is said peak energy; and
   (b) analyzing said peak energy and converting said peak energy into different exercising data which are selected from a group consisting of an energy consumption data of the user in form of calories, step data, a step balancing analysis data, a weight analysis data, and a user weight identification data, wherein, in the step (b), said energy consumption data is converted from said peak energy from said motor to calculate how many calories the user burnt in response to said peak energy.

2. An energy analyzing method for an exercise machine, which comprises the steps of:
   (a) collecting a peak energy from a motor of said exercise machine in response to a dragging force on a belt of said exercise machine, wherein said peak energy is collected by the steps of:
   (a.1) determining an initial energy from said motor to maintain said belt at a constant speed when said motor is in an idle position; and
   (a.2) determining an additional energy from said motor to maintain said belt at said constant speed when said dragging force is applied on said belt, wherein said additional energy from said motor is said peak energy; and
   (b) analyzing said peak energy and converting said peak energy into different exercising data which are selected from a group consisting of an energy consumption data of the user in form of calories, step data, a step balancing analysis data, a weight analysis data, and a user weight identification data, wherein, in the step (b), said step data is converted by a detection of said dragging force on said belt that a speed sensor collects a step signal from each step of the user and combine said step signals to a feedback signal, such that said feedback signal includes a frequency of said step signal and a value of each step signal, wherein said frequency of said speed signal is defined by a frequency of the steps provided by the user's right and left feet.

3. The energy analyzing method, as recited in claim 2, wherein the step (b) further comprises a step of calculating total number of steps within a period of time in response to said step signal.

4. The energy analyzing method, as recited in claim 2, wherein the step (b) further comprises a step of measuring a value of weight provided by each step of the user's right and left feet, wherein said step signal from each step includes the value of each step signal, so that the values of said step signal are calculated to be an amount of forces provided by the user's right and left feet.

5. The energy analyzing method, as recited in claim 2, wherein the step (b) further comprises a step of calculating a weight of the user.

6. The energy analyzing method, as recited in claim 2, wherein the step (b) further comprises a step of identifying the user by a weight of the user.

* * * * *